United States Patent [19]

Quiroz

[11] Patent Number: 4,875,490
[45] Date of Patent: Oct. 24, 1989

[54] INTRAVAGINAL DEVICE

[76] Inventor: Roberto Quiroz, 341 Lucerno La., El Paso, Tex. 79917

[21] Appl. No.: 240,805

[22] Filed: Sep. 6, 1988

[51] Int. Cl.$^4$ ............................................... A61F 13/00
[52] U.S. Cl. ................................... 128/830; 128/842; 128/844
[58] Field of Search ...................... 128/830, 831, 832

[56] References Cited

U.S. PATENT DOCUMENTS

| 2,591,783 | 4/1952 | Craddock | 128/842 |
| 3,536,066 | 10/1970 | Ludwig | 128/830 |
| 4,664,104 | 5/1987 | Jaicks | 128/830 |

Primary Examiner—Robert A. Hafer
Assistant Examiner—Charles H. Sam
Attorney, Agent, or Firm—Pravel, Gambrell, Hewitt, Kimball & Krieger

[57] ABSTRACT

Herein presented is an intravaginal device to shield against contact with communicable infections and diseases. The device is an elastic container. The container functions similar to a condom but it can completely cover both the female and and male genitalia. The device can contain lubricant jelly and its exterior is covered with lubricant jelly. The elastic nature of the device allows it to conform to the surface shapes of the vagina and penis as the penis penetrates and enters into the vagina. The device is easy to use and completely disposable.

4 Claims, 3 Drawing Sheets

INTRAVAGINAL DEVICE

BACKGROUND OF THE INVENTION

Mankind is sexually active. Although artificial means for reproduction have been found, mankind's existence still depends on his sexual reproductive activities. Mankind has experienced a population explosion. He has also experienced an explosion in communicable diseases. Some of these diseases are deadly. One such disease Acquired Immunity Deficiency Syndrome is at this time spreading at an alarming rate and is incurable. The device presented here is to aid in the prevention of the spread of venereal diseases. The device is similar to the condom, but it also differs from the condom in many aspects. The device is made of the same elastic materials as the materials used to make the condom. The condom is physically designed, and used, to cover the male penis. And its main function is to prevent lesions, infections and fluids on and from the penis from coming in contact with the female. The surface area covered by the condom is small. The high rate of breakage and failure of the condom has been widely reported. The device presented here covers the female genitalia and vagina. A version of the device presented here covers the entire areas of both the male and female genitalia. This greatly increases the protection. Even if the covering over the male's organ breaks or fails, the female's covering will still prevent contact and infection.

SUMMARY OF THE INVENTION

The device presented here is an elastic container which will cover and protect the surface of the female genitalia during sexual intercourse. The elastic nature of the device allows it to assume the shape of the female genitalia. The device has a number of versions all of which are derived from its basic shape. In its simplest form, it is an elongated bag. This elastic, elongated bag is placed in the vagina. Its exterior surface contact and covers the inner surface of the vagina. It assumes the changing shape of the vagina during sexual intercourse.

Another version provides covering for the external genitalia. The extended length of the elongated bag provides cover for the lips, clitoris, external urethral orifice and parts of the labia majora and minora.

In yet another version of the device, the container is closed and it consist of two elongated bulbs. Its shape is similar to a figure eight. There are no barrier separating the two bulbs. One bulb is large and is the same as the above described elongated bag that is placed in the vagina. The other is smaller and is similar to a condom. It is initially lying outside the vagina while the larger bulb is placed in the vagina. The penis in penetrating the vagina comes in contact with the exterior surface of this smaller bulb and the exterior surface covers the penis. The penis pushes the interior surface into the larger bulb. When the penis is in the vagina its surface is covered by the exterior surface of the small bulb and the inner surface of the vagina is covered by the exterior surface of the larger bulb. So two layers of the elastic container separate the penis and its fluids from the inner surface of the vagina. A final version provides the closed container having the two elongate bulbs with the additional covering for the external genitalia. All versions have lubricating jellies.

BRIEF DESCRIPTION OF THE DRAWINGS

The invention can be better understood by examining the following in connection with the accompanying drawings, to wit.

DESCRIPTION OF THE PREFERRED EMBODIMENTS

Figure 1:
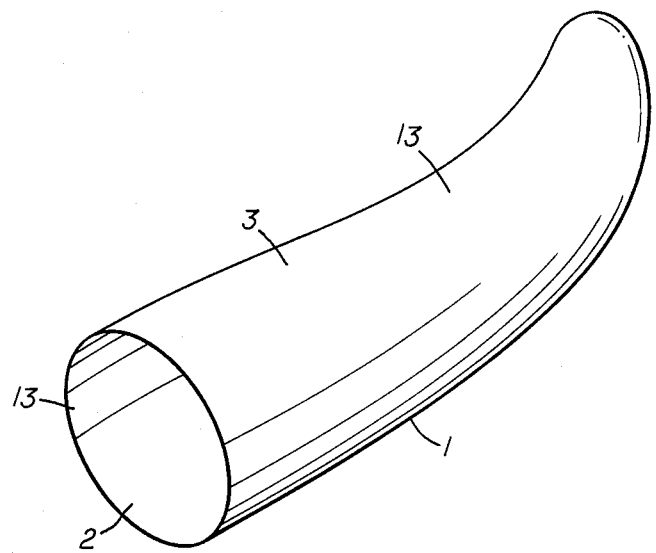
FIG. 1 is a plan view of the simplest version of the device.

Referring now to the drawings, the preferred embodiments of the invention are ilustrated in FIGS. 1-6. FIG. 1 shows the simplest form of the invention. It is an elongated, elastic bag (1). It has an opening (2) and an external surface (3). The bag (1) is placed inside the vagina. During sexual intercourse the penis enters the opening (2); and the external surface (3) of the bag covers the surface of the vagina protecting it from contact with the penis and its fluids. A means for supporting and holding the bag (1) in the vagina is not shown.

Figure 2:
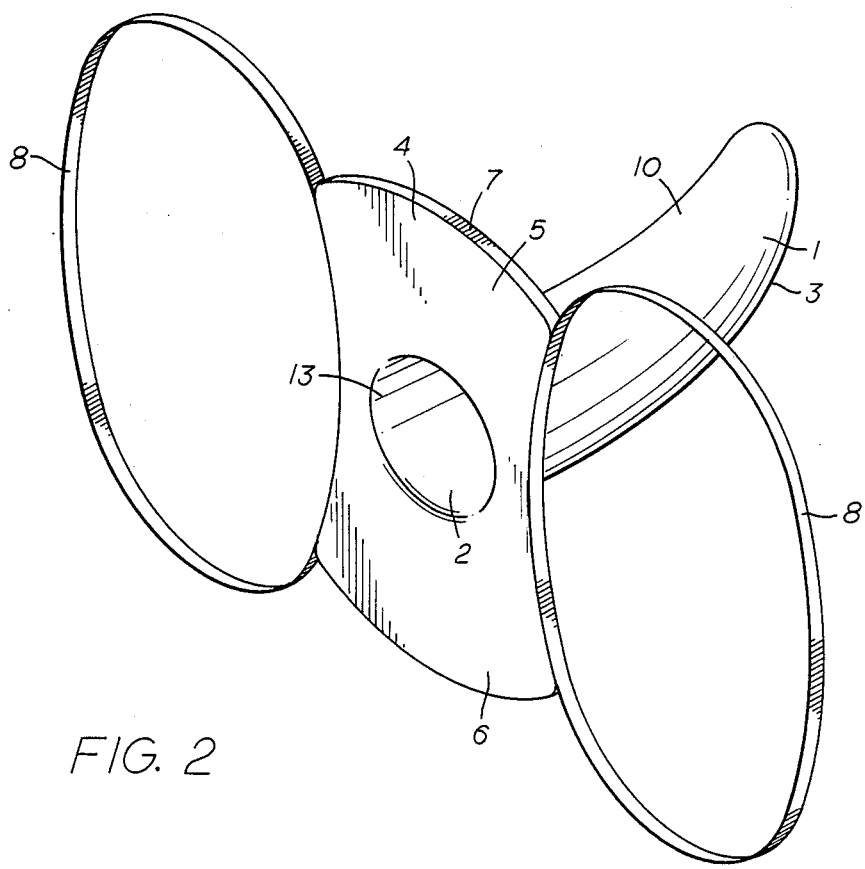
FIG. 2 is a plan view of a version of the device having a covering for the external genitalia.
Figure 4:
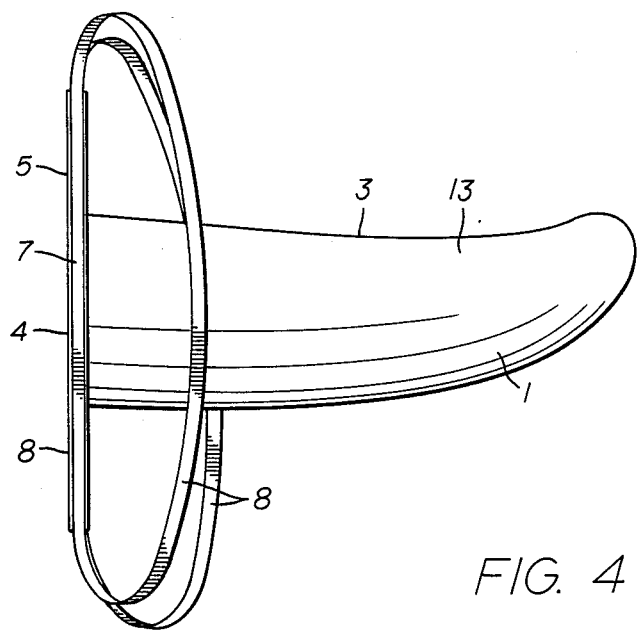
FIG. 4 is a side view of FIG. 3.
Figure 3:
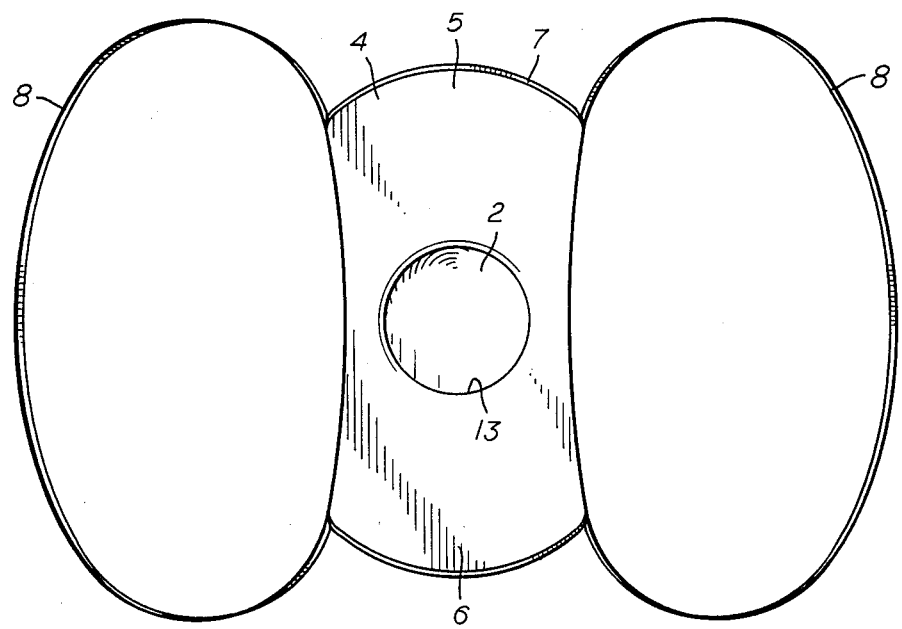
FIG. 3 is a front view of FIG. 2.

FIGS. 2, 3 and 4 show the device with coverings (4) for the external genitalia. The original device of FIG. 1 has been lengthen so that the elastic covering extends out of the vagina. The portion extending out of the vagina has been divided into an upper covering (5) and a lower covering (6). An elastic band (7) runs the perimeter of these covers (4). Also elastic straps (8) have been added to assist in supporting and holding the bag (1) and covering (4). A leg fits into each strap and the strap is pulled up over the leg.

Figure 5:
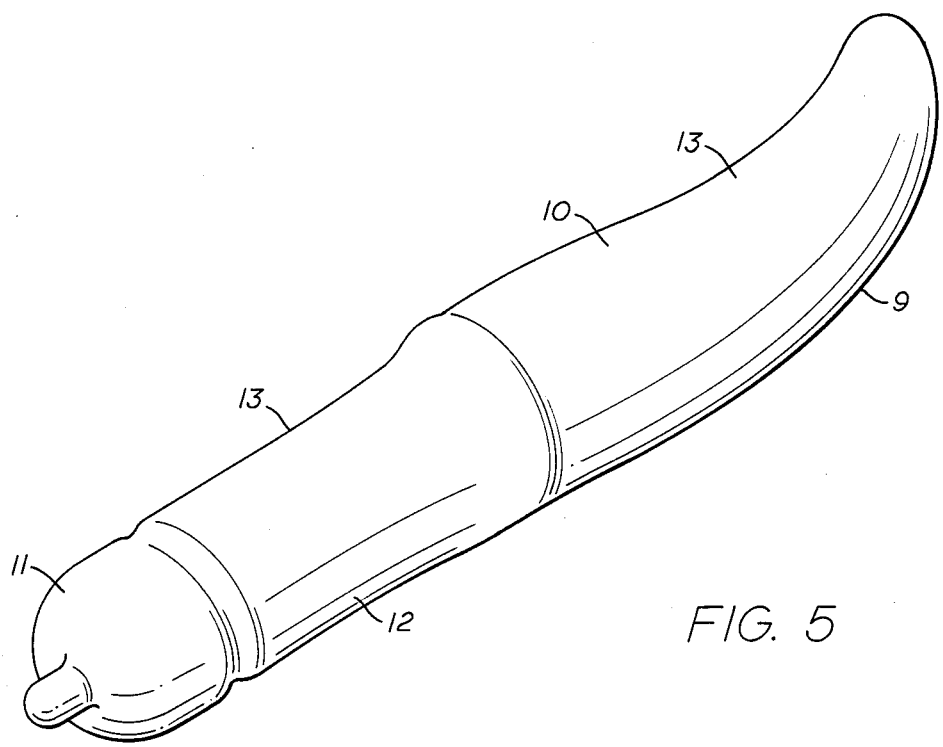
FIG. 5 is a plan view of the closed device having two elongated bulbs.

FIG. 5 shows another version of the device. This version has no opening. It has a shape similar to a figure eight. Each end of the bag is an elongated bulb. One end (9) is the same shape and size as the elastic bag presented in FIG. 1. This end (9) is placed in the vagina. Its external surface (10) covers the surface of the vagina. The other end (11) is smaller and is the shape and size of a standard condom. The penis in penetrating the vagina comes in contact with the exterior surface (12) of the smaller elongated bulb. This exterior surface (12) covers the penis as the penis enters into the vagina. No means for holding the device in place are shown.

Figure 6:
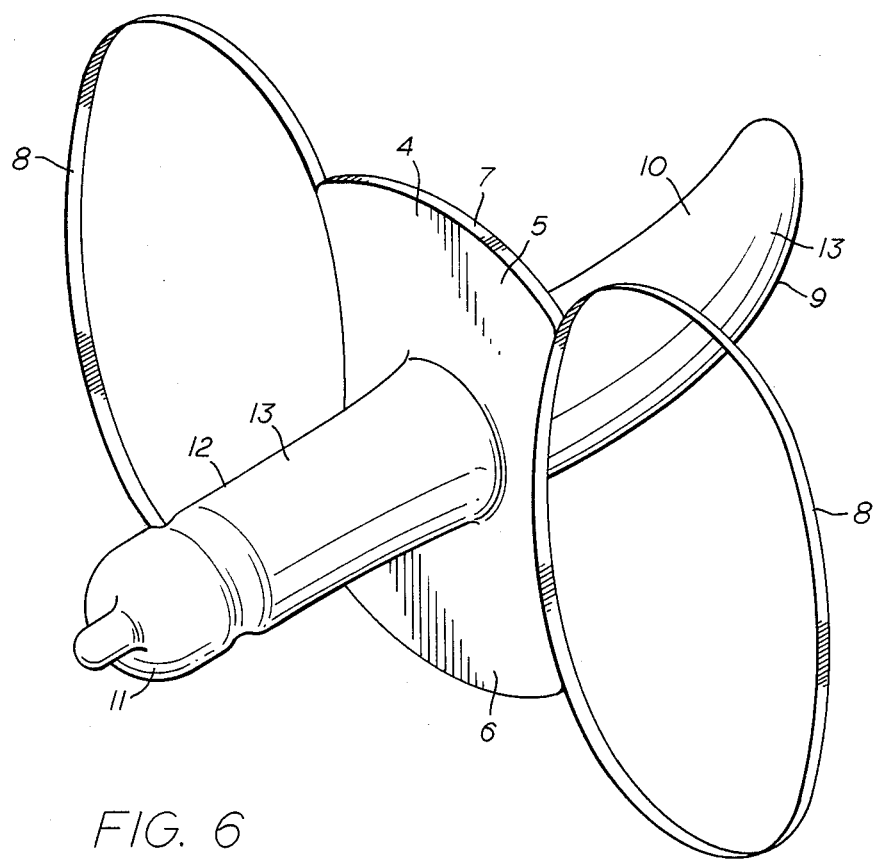
FIG. 6 is a plan view of the device in FIG. 5 but having also a covering for the external genitalia.

Finally, FIG. 6 shows the device described in FIG. 5 with the coverings (4) and straps (8) described in FIGS. 2, 3 and 4. All versions of the device come with lubricating jellies (13).

While the invention has been shown and described with reference to the preferred embodiments thereof, it will be understood by those skilled in the art that various changes in form and details may be made therein without departing from the spirit and scope of the invention.

What is claimed is:

1. An intravaginal device comprising an elongated and elastic closed bag, one end of said bag fitting into the female vagina and covering the surface of the vagina during sexual intercourse, a second end of the said elongated, elastic bag being the size and shape of a standard condom, said second end initially extending outside of the vagina and its exterior surface and covering the penis as it enters the vagina.

2. An intravaginal device as in claim 1 wherein a means for holding and supporting the said elastic bag in place is provided.

3. An intravaginal device as in claim 1 wherein an upper portion and a lower portion, attached to the portion of said elastic bag where it extends out of the vagina, cover the external genitalia, an elastic band running the parameters of said upper portion and said lower portion.

4. An intravaginal device as in claim 3 wherein a means for holding and supporting the said elastic bag and upper portion and lower portion in place is provided.

* * * * *